(12) United States Patent
Sano

(10) Patent No.: US 6,600,167 B2
(45) Date of Patent: Jul. 29, 2003

(54) MEDIUM DISCERNING APPARATUS WITH OPTICAL SENSOR

(75) Inventor: Masashi Sano, Kyoto (JP)

(73) Assignee: Rohm Co., Ltd., Kyoto (JP)

(*) Notice: Subject to any disclaimer, the term of this patent is extended or adjusted under 35 U.S.C. 154(b) by 0 days.

(21) Appl. No.: 09/877,101

(22) Filed: Jun. 11, 2001

(65) Prior Publication Data

US 2002/0005497 A1 Jan. 17, 2002

(30) Foreign Application Priority Data

Jun. 12, 2000 (JP) .................................... 2000-174651

(51) Int. Cl.[7] .......................... G01N 21/86; G01N 8/00
(52) U.S. Cl. ............................. 250/559.11; 250/559.4; 347/106
(58) Field of Search .................... 250/559.11, 559.12, 250/559.15, 221, 559.39–559.46; 355/41; 356/239.2, 239.7; 399/389; 400/708; 347/19, 106

(56) References Cited

U.S. PATENT DOCUMENTS

| | | | | |
|---|---|---|---|---|
| 4,540,887 A | * | 9/1985 | Minerd et al. | ......... 250/223 R |
| 4,650,990 A | * | 3/1987 | Jonsson | ..................... 250/221 |
| 5,139,339 A | * | 8/1992 | Courtney et al. | ........ 250/341.8 |
| 6,018,164 A | * | 1/2000 | Mullens | .................. 250/559.4 |
| 6,170,747 B1 | * | 1/2001 | Meyer | ........................ 235/436 |

FOREIGN PATENT DOCUMENTS

| JP | 2-056375 | 2/1990 | ........... B65H/43/08 |
|---|---|---|---|
| JP | 10-198174 | 7/1998 | ........... G03G/15/08 |

* cited by examiner

Primary Examiner—David Porta
Assistant Examiner—Stephen Yam
(74) Attorney, Agent, or Firm—Michael D. Bednarek; Shaw Pittman LLP

(57) ABSTRACT

An optical sensor includes a light-emitting element and first to third light-receiving elements. The light-emitting element is arranged on a first side of a transfer path along which a recording sheet is moved. The first light-receiving element is arranged on a second side of the transfer path which is opposite to the first side. The second and the third light-receiving elements are arranged on the first side of the transfer path in the vicinity of the light-emitting element.

8 Claims, 4 Drawing Sheets

MEDIUM DISCERNING APPARATUS WITH OPTICAL SENSOR

BACKGROUND OF THE INVENTION

1. Field of the Invention

The present invention generally relates to an optical sensing technique for discerning the types of objects or mediums based on their interaction with light. In particular, the present invention relates to an apparatus for discerning different kinds of recording sheets (plain paper, glossy paper, transparent sheets, etc.) from each other.

2. Description of the Related Art

Electrophotographic printers or copiers have been widely used for printing desired information on recording mediums, such as plain paper, glossy (or slick) paper and transparent plastic sheets (as used for overhead projectors or OHPs). To perform proper printing on these different types of recording sheets by an electrophotographic printer; it may be necessary to alter the print settings of the printer in accordance with the nature of the selected recording medium. For instance, to properly transfer toner-developed images from the photosensitive drum to a recording sheet, it may be necessary to increase or decrease the applied voltage, depending upon whether the recording sheet is a plain paper sheet or transparent plastic sheet (called "OHP sheet" below). Further, it may also be necessary to change the feeding speed of a recording sheet in passing through the fixing unit of the printer. Specifically, the feeding speed of an OHP sheet may need to be made slower than that of a plain paper sheet, so that the transferred toner images take sufficient time to melt properly, thereby obtaining great transparency.

To make efficient adjustments of the toner transfer voltage or sheet feeding speed described above, it is convenient if the types of the selected printing medium are automatically determined. Along this line, various kinds of automatic sensing techniques have been conventionally proposed.

For instance, JP-A-2 (1990)-56375 discloses a medium detecting device which utilizes an optical sensor. Specifically, as shown in FIG. 4 of the accompanying drawings, the conventional device is provided with an optical sensor 8 which includes one light-emitting unit 80 cooperating with two (or more) light-receiving units 81, 82.

The light-emitting unit 80 is arranged so that its center line makes a rather large angle $\theta(=60°-75°)$ with the normal line of the recording sheet S. The rays of light emitted from the unit 80 will partly be reflected regularly and partly be diffused at the point O on the recording sheet S. On the opposite side of the normal line, the first light-receiving unit 81 is arranged so that its center line makes the same angle $\theta$ with the normal line. Thus, the rays of light regularly reflected on the sheet S will be received by the first light-receiving unit 81.

The second light-receiving unit 82 is disposed at a higher position and closer to the normal line than the first unit 81 is. Thus, the angle $\phi$ made between the normal line of sheet S and the center line of the unit 82 is smaller than the above-mentioned angle $\theta$. With this arrangement, part of the light diffused at the point O on the sheet S will be received by the second unit 82.

The above conventional medium detecting device can distinguish one type of recording medium from another in the following manner.

When the recording medium S is plain paper, the light emitted from the unit 80 is diffused at the point O. Then, the diffused light will be received partly by the first light-receiving unit 81 and partly by the second light-receiving unit 82. Accordingly, both the first and the second units 81, 82 will output detection signals of similar or same strengths.

When the recording medium S is glossy paper, on the other hand, the light emitted from the unit 80 tends to be reflected regularly at the point O on the sheet S. Thus, most of the reflected light is received by the first unit 81, whereas only a small portion of the reflected light is received by the second unit 82. Accordingly, a strong detection signal will be outputted from the first unit 81, while a weak detection signal will be outputted from the second unit 82.

Thus, it is possible to determine whether the recording medium S is plain paper or glossy paper by monitoring the detection signals outputted from the first and the second light-receiving units 81, 82.

While the conventional device is functional in the above manner, it suffers from the following drawback.

As stated above, the conventional device can distinguish two types of recording paper (plain paper and glossy paper). However, since its distinction is based only on reflection light, it is difficult or substantially impossible for the conventional device to distinguish glossy paper and a transparent plastic sheet (used for e.g. an overhead projector) both of which have a slick surface, thereby regularly reflecting light from the unit 80 in the same manner. This means that the conventional device cannot make a correct distinction when the recording mediums to be used include three types of material such as plain paper, glossy paper and transparent sheets.

A second example of conventional medium detecting device is disclosed in JP-A-10(1998)-198174. The device includes one light-receiving unit for two or more light-emitting units. However, as in the above-described first conventional device, the second device can only distinguish two types of material such as plain paper and transparent OHP sheets, but cannot three types of material (plain paper, glossy paper and transparent sheets).

SUMMARY OF THE INVENTION

The present invention has been proposed under the circumstances described above. It is, therefore, an object of the present invention, to provide a sensing technique which makes it possible to distinguish at least three types of recording mediums such as plain paper, glossy paper and transparent sheets.

According to the present invention, there is provided an optical sensor which includes: a light-emitting element arranged on a first side of a transfer path along which an object is moved; a first light-receiving element arranged on a second side of the transfer path, the second side being opposite to the first side; a second light-receiving element arranged on the first side of the transfer path; and a third light-receiving element arranged on the first side of the transfer path.

Preferably, the transferred object maybe any one of plain paper, glossy paper and transparent plastic sheet.

Preferably, the light-emitting element may have a light output surface, while the first light-receiving element may have a light input surface facing the light output surface.

Preferably, the third light-receiving element may be spaced farther from the light-emitting element than the second light-receiving element is. In this case, the distance between the light-emitting element and the second light-receiving element may be smaller than the distance between the second and the third light-receiving elements.

Preferably, the light-emitting element may be disposed between the second and the third light-receiving elements.

Preferably, the light-emitting element, the second light-receiving element and the third light-receiving element may be disposed at substantially the same distance from the transfer path.

Preferably, each of the second and the third light-receiving elements may have a light input surface which is skew to the transfer path.

Preferably, the sensor of the present invention may further include a first discerning unit and a second discerning unit, wherein the first discerning unit is connected to the first light-receiving element, and the second discerning unit is connected to both the second and the third light-receiving elements.

Preferably, the second discerning unit may detect the difference in amount of received light between the second and the third light-receiving elements.

Preferably, the sensor of the present invention may further include a common casing which holds the light-emitting element and the second and the third light-receiving elements.

Other features and advantages of the present invention will become apparent from the detailed description given below with reference to the accompanying drawings.

DETAILED DESCRIPTION OF THE PREFERRED EMBODIMENTS

The preferred embodiments of the present invention will be described below with reference to the accompanying drawings.

Figure 1:
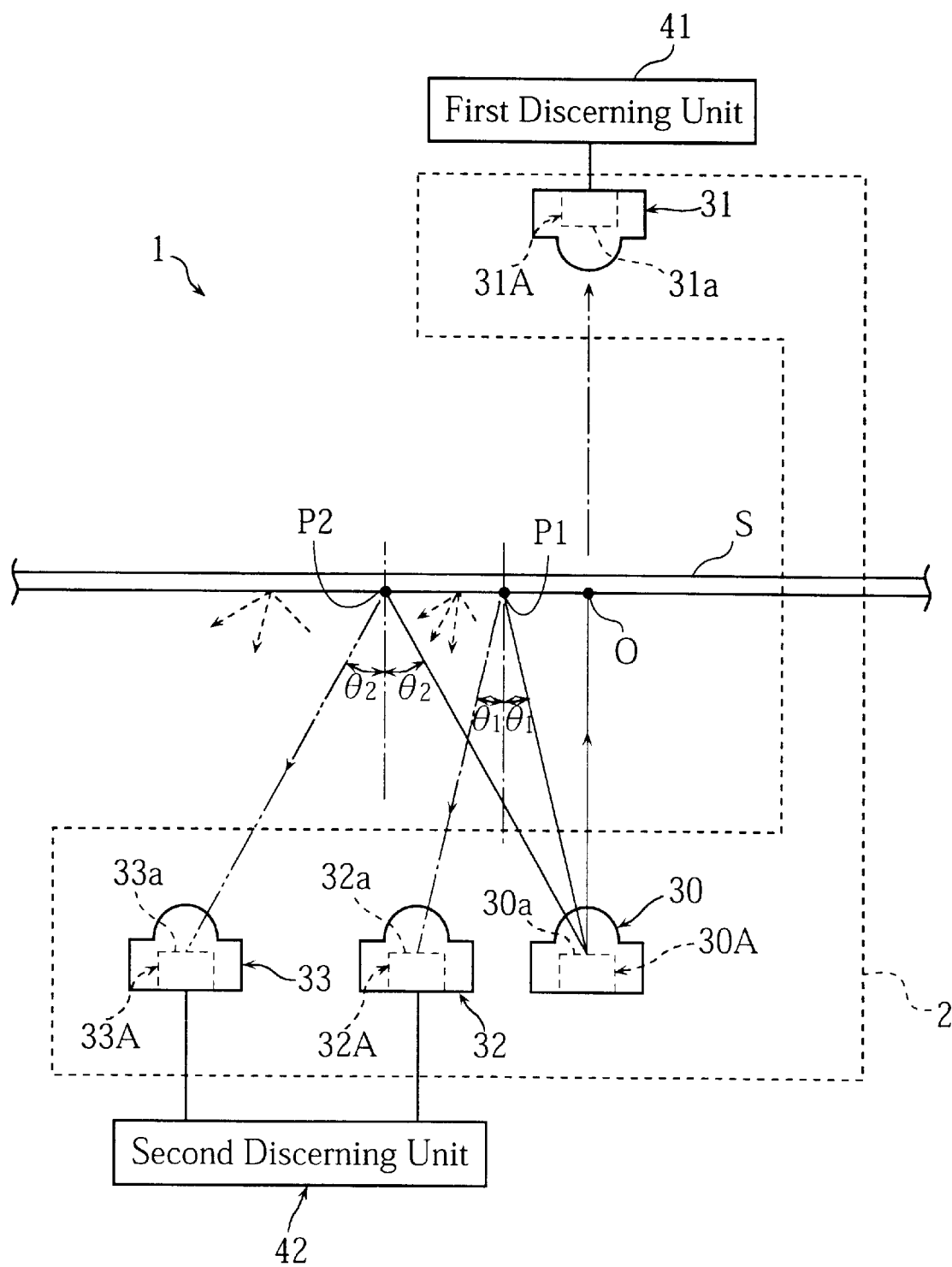
FIG. 1 shows the principal components of an optical sensor embodying the present invention.

FIG. 1 schematically shows principal components of a recording sheet discerning apparatus (generally indicated by reference 1) according to the present invention. The discerning apparatus 1 may be incorporated in an electrophotographic color copier to automatically determine the type of the selected recording sheet S. In accordance with this determination, the copier may select a print mode suitable for the type of the recording sheet S.

In the illustrated embodiment, the type of the recording sheet S is any one of plain paper, glossy paper and transparent sheet used for an overhead projector (OHP). As will be described below, plain paper and glossy paper are distinguished from an OHP sheet by their opacity. Plain paper is distinguished from glossy paper by its greater tendency to cause diffusion of light.

As shown in FIG. 1, the discerning apparatus 1 includes an optical sensor 2, a first discerning circuit 41 and a second discerning circuit 42. The sensor 2 includes a light-emitting unit 30, a first light-receiving unit 31, a second light-receiving unit 32 and a third light-receiving unit 33.

As illustrated, the light-emitting unit 30 has a light-emitting surface 30a which faces a recording sheet S moved along the predetermined sheet transfer path. The first light-receiving unit 31 is arranged at a position opposite to the light-emitting unit 30 with respect to the sheet transfer path. The first light-receiving unit 31 has a light-receiving surface 31a facing the light-emitting surface 30a of the unit 30. The line connecting between the light-emitting surface 30a and the light-receiving surface 31a perpendicularly intersects the sheet transfer path at a point O.

The second and third light-receiving units 32, 33 are disposed on the same side of the sheet transfer path as the light-emitting unit 30. In the illustrated embodiment, the three units 30, 32 and 33 are disposed at the substantially same distance from the transfer path. The second and third light-receiving units 32, 33 have light-receiving surfaces 32a and 33a, respectively, which are held in facing relation to the recording sheet S. These two units 32 and 33 are offset from the light-emitting unit 30 along the sheet transfer path (to the left in FIG. 1). As seen from FIG. 1, the distance between the unit 30 and the unit 32 is smaller than the distance between the unit 32 and the unit 33. Thus, the second light-receiving unit 32 receives light which is regularly reflected at a point P1 (incidence and reflection angles θ1). Similarly, the third light-receiving unit 33 receives light which is regularly reflected at a point P2 (incidence and reflection angles θ2). The angle θ2 is greater than the angle θ1.

Figure 2:
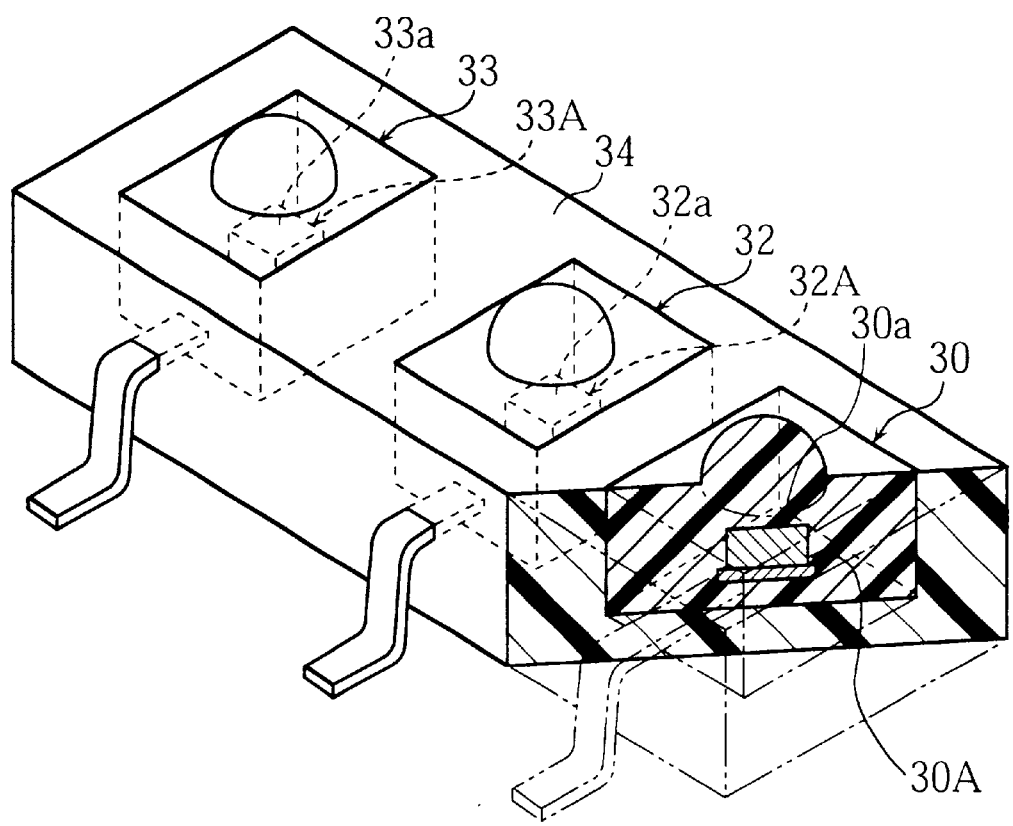
FIG. 2 shows a casing of the sensor in which one light-emitting element and two light-receiving elements are embedded.

The light-emitting unit 30 includes an LED (light-emitting diode) chip enclosed by a resin coating, as shown in FIG. 2. The second and third light-receiving units 32, 33 include semiconductor light-receiving elements 32A and 33A, respectively. Each of the elements 32A, 33A is also enclosed by a resin coating. The light-emitting unit 30 and the second and third light-receiving units 32, 33 are held together by a common resin casing 34. Turning back to FIG. 1, the first light-receiving unit 31 includes a semiconductor light-receiving element 31A enclosed by a resin coating.

The rays of light emitted from the unit 30 are nonparallel, spreading outward as they travel (see FIG. 1). In addition, the intensity of light is greater as the rays are inner or closer to the central axis of the light cone. Thus, supposing that all the rays are reflected regularly (nondiffused reflection) on the recording sheet S, the second light-receiving unit 32 receives stronger light (reflected at point P1) than the third light-receiving unit 33, which receives light reflected at point P2. Accordingly, the detection signal outputted from the second light-receiving unit 32 is stronger than the detection signal outputted from the third light-receiving unit 33, which results in a great difference between the two detection signals (refered to as "first case" below).

On the other hand, supposing that there occurs some diffusion of light on the recording sheet S, part of light meeting the sheet S at point P1 is diffused, so that the second light-receiving unit 32 receives less amount of light than in the "first case." Contrarily, the third light-receiving unit 33 receives more light due to the light diffusion. Thus, in this case ("second case"), the difference in the amount of received light between the second and the third light-receiving units 32, 33 becomes smaller than in the first case. Thus, by discerning the first and the second cases, it is possible to determine whether the recording sheet S is of the type prone to light diffusion or proper reflection.

The first and second discerning units 41, 42 may include a ROM (read-only memory), a RAM (random-access memory), and a CPU (central processing unit). The ROM may store programs required for detecting the presence of a recording sheet and for discerning, if any, the type of the recording sheet, based on the amount of received light. The RAM may temporarily store data for performing required calculations. The CPU may execute the programs for detecting the presence or discerning the type of the recording sheet.

Specifically, upon finding that the amount of light received by the first light-receiving unit 31 is no less than a predetermined reference value RV, the first discerning unit 41 determines that no opaque recording sheet S exists between the light-emitting unit 30 and the first light-receiving unit 31. In this case, there are two possibilities: (1) No recording sheet exists between the units 30 and 31. (2) A transparent OHP sheet exists between the units 30 and 31.

When there is no recording sheet at all, the light emitted from the unit 30 is unimpededly received by the first light-receiving unit 31. On the other hand, when a transparent OHP sheet exists, part of the light emitted from the unit 30 is reflected by the OHP sheet, while most of the light passes through the OHP sheet to be received by the first light-receiving unit 31. This means that the first light-receiving unit 31 receives different amounts of light, depending on whether an OHP sheet exists or not. Thus, by detecting this difference, it is possible to determine that the supplied recording medium is an OHP sheet, or that no recording sheet exists between the light-emitting unit 30 and the first light-receiving unit 31.

When the first light-receiving unit 31 receives an amount of light which is less than the above-mentioned reference value RV, the first discerning unit 41 determines that there exists an opaque recording sheet S between the units 30 and 31. In this case, the recording sheet S is either plain paper or glossy paper.

The decision about whether the sheet S is plain paper or glossy paper is made by the second discerning unit 42. The plain paper is coarser than the glossy paper, thereby being more liable to diffuse light. Conversely, the glossy paper tends to reflect light regularly (that is, the angle of incidence is equal to the angle of reflection). As previously described, the difference in amount of received light between the second and the third light-receiving units 32, 33 becomes relatively small when the sheet S is liable to diffuse light, whereas it becomes relatively great when the sheet S is liable to cause proper reflection. Thus, by calculating the difference of received light, the second discerning unit 42 determines that the sheet S is plain paper when the difference is small (namely, below a prescribed threshold). When the difference is great (no less than the prescribed threshold), the second unit 42 determines that the sheet S is glossy paper.

As described above, the discerning apparatus 1 of the present invention distinguishes three kinds of recording sheets (plain paper, glossy paper and a transparent sheet) from each other. This is advantageous over the prior art devices which are capable of distinguishing only two kinds of recording sheets.

Further, according to the present invention, the second discerning unit 42 makes a distinction between the plain paper and the glossy paper in accordance with a relative value, that is, the difference in amount of light received by the second and the third light-receiving units 32, 33. This is advantageous in the following respect. The light-emitting unit 30, incorporating an LED, may degenerate with time, thereby failing to keep providing the initial amount of illumination light toward the recording sheet S. When this happens, the second and the third light-receiving units 32, 33 will receive a smaller amount of light, thereby outputting a weaker detection signal than before. In the discerning apparatus 1 of the present invention, however, the difference in amount of light received by the second and the third light-receiving units 32, 33 is monitored to make the required decision. The difference is a relative value and therefore will not vary significantly even when the emission of light by the unit 30 is reduced. Thus, based on thid difference, it is possible to perfrom the determination of the sheet type correctly.

Figure 3A:
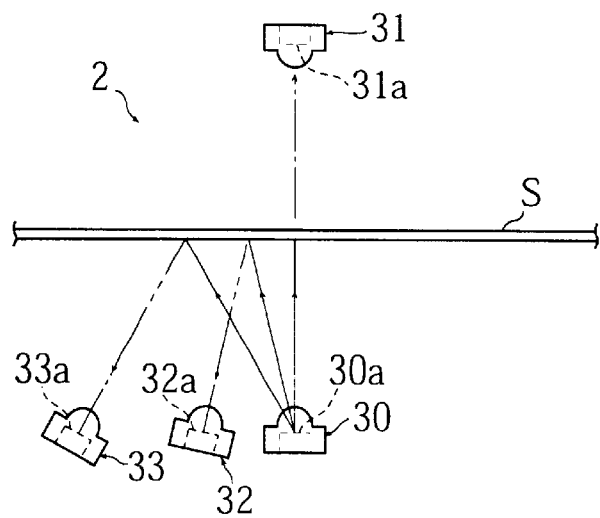
FIGS. 3A–3C show possible layouts of the optical elements used for the sensor of the present invention.
Figure 3B:
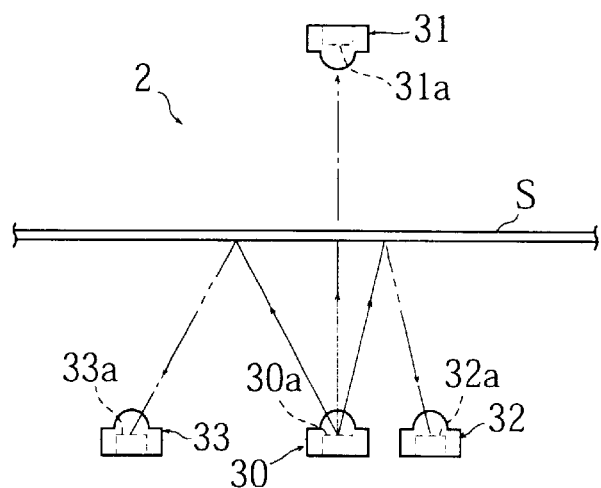
Figure 3C:
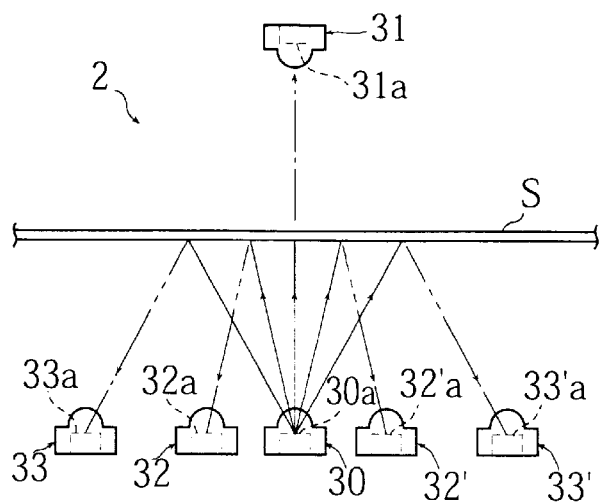
Figure 4:
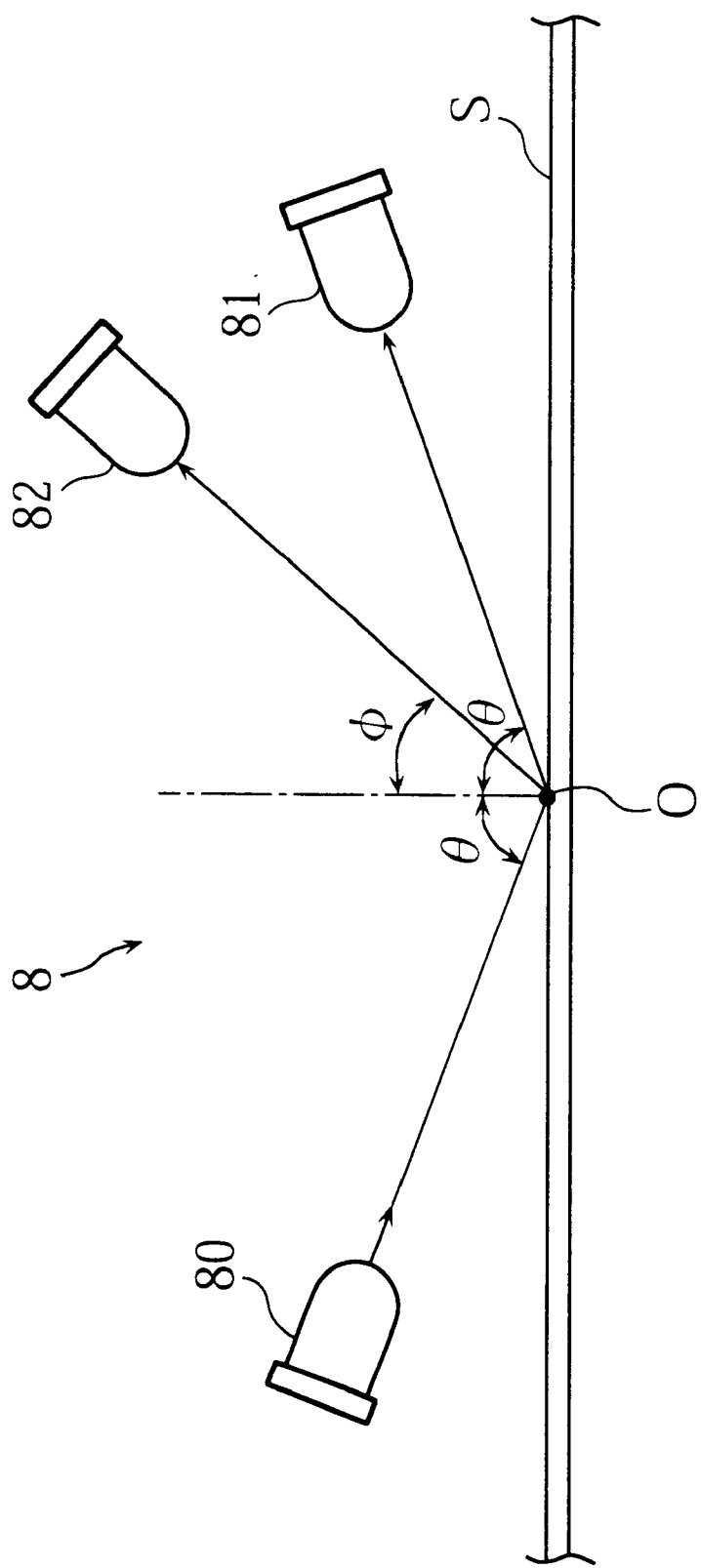
FIG. 4 shows the principal components of a conventional medium detecting device.

In the above-described embodiment, the light-emitting unit 30 and the second and third light-receiving units 32, 33 are arranged on the square with respect to the recording sheet S. The present invention, however, is not limited to this. For instance, as shown in FIG. 3A, the second and third light-receiving units 32, 33 may be skew relative to the sheet S. As shown in FIG. 3B, the second light-receiving unit 32 may be arranged opposite to the third light-receiving unit 33 with respect to the light-emitting unit 30. Further, as shown in FIG. 3C, use may be made of additional second and third light-receiving units 32', 33'. These additional units may preferably be arranged symmetrically to the original second and third units 32, 33 with respect to the center line connecting between the light-emitting unit 30 and the first light-receiving unit 31.

The present invention being thus described, it is obvious that the same may be varied in many ways. Such variations are not to be regarded as a departure from the spirit and scope of the present invention, and all such modifications as would be obvious to those skilled in the art are intended to be included within the scope of the following claims.

What is claimed is:

1. An optical sensor comprising:
    a light-emitting element arranged on a first side of a transfer path along which a sheet to be discerned as to its type is moved;

a first light-receiving element arranged on a second side of the transfer path for detecting light which passes through the sheet, the second side being opposite to the first side;

a second light-receiving element arranged on the first side of the transfer path for detecting part of light reflected on the sheet;

a third light-receiving element arranged on the first side of the transfer path for detecting part of light reflected on the sheet; and a common resin casing accommodating the light-emitting element, the second light-receiving element and the third light-receiving element;

wherein the light-emitting element, the second light-receiving element and the third light-receiving element are equally oriented in a same direction;

wherein the resin casing is provided with a plurality of lead terminals projecting out of the resin casing.

2. The sensor according to claim 1, wherein the light-emitting element has a light output surface, the first light-receiving element having a light input surface facing the light output surface.

3. The sensor according to claim 1, wherein the third light-receiving element is spaced farther from the light-emitting element than the second light-receiving element is.

4. The sensor according to claim 3, wherein a distance between the light-emitting element and the second light-receiving element is smaller than a distance between the second and the third light-receiving elements.

5. The sensor according to claim 1, wherein the light-emitting element is disposed between the second and the third light-receiving elements.

6. The sensor according to claim 1, wherein the light-emitting element, the second light-receiving element and the third light-receiving element are disposed at a substantially same distance from the transfer path.

7. The sensor according to claim 1, further comprising a first discerning unit and a second discerning unit, the first discerning unit being connected to the first light-receiving element, the second discerning unit being connected to both the second and the third light-receiving elements.

8. The sensor according to claim 7, wherein the second discerning unit detects a difference in amount of received light between the second and the third light-receiving elements.

* * * * *